(12) United States Patent
Klopman et al.

(10) Patent No.: US 8,329,756 B2
(45) Date of Patent: Dec. 11, 2012

(54) DRUG FOR TREATMENT OF COLON CANCER

(75) Inventors: Gilles Klopman, Sarasota, FL (US); Suman K. Chakravarti, Beachwood, OH (US)

(73) Assignee: Oncophor, LLC, Beachwood, OH (US)

( * ) Notice: Subject to any disclaimer, the term of this patent is extended or adjusted under 35 U.S.C. 154(b) by 0 days.

(21) Appl. No.: 12/974,021

(22) Filed: Dec. 21, 2010

(65) Prior Publication Data

US 2011/0257270 A1    Oct. 20, 2011

Related U.S. Application Data

(60) Provisional application No. 61/288,517, filed on Dec. 21, 2009.

(51) Int. Cl.
*A61K 31/136* (2006.01)
*A61K 31/137* (2006.01)

(52) U.S. Cl. .................................... 514/649; 514/655

(58) Field of Classification Search .................. None
See application file for complete search history.

(56) References Cited

OTHER PUBLICATIONS

McMillan et al., British Journal of Cancer, (2010), 103(7), pp. 970-974.*

* cited by examiner

*Primary Examiner* — Phyllis G. Spivack
(74) *Attorney, Agent, or Firm* — Fay Sharpe LLP

(57) ABSTRACT

The invention provides a method for treating or ameliorating colon cancer in a mammal comprising administering to the mammal a therapeutically effective amount of one or more compounds selected from the group consisting of compounds of Formula (1), (2), and a pharmaceutically acceptable salt or metabolite thereof.

Formula (1)

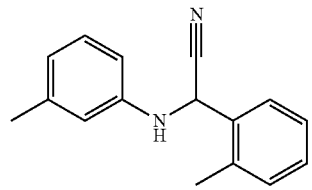

Formula (2)

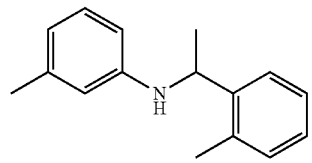

9 Claims, 1 Drawing Sheet

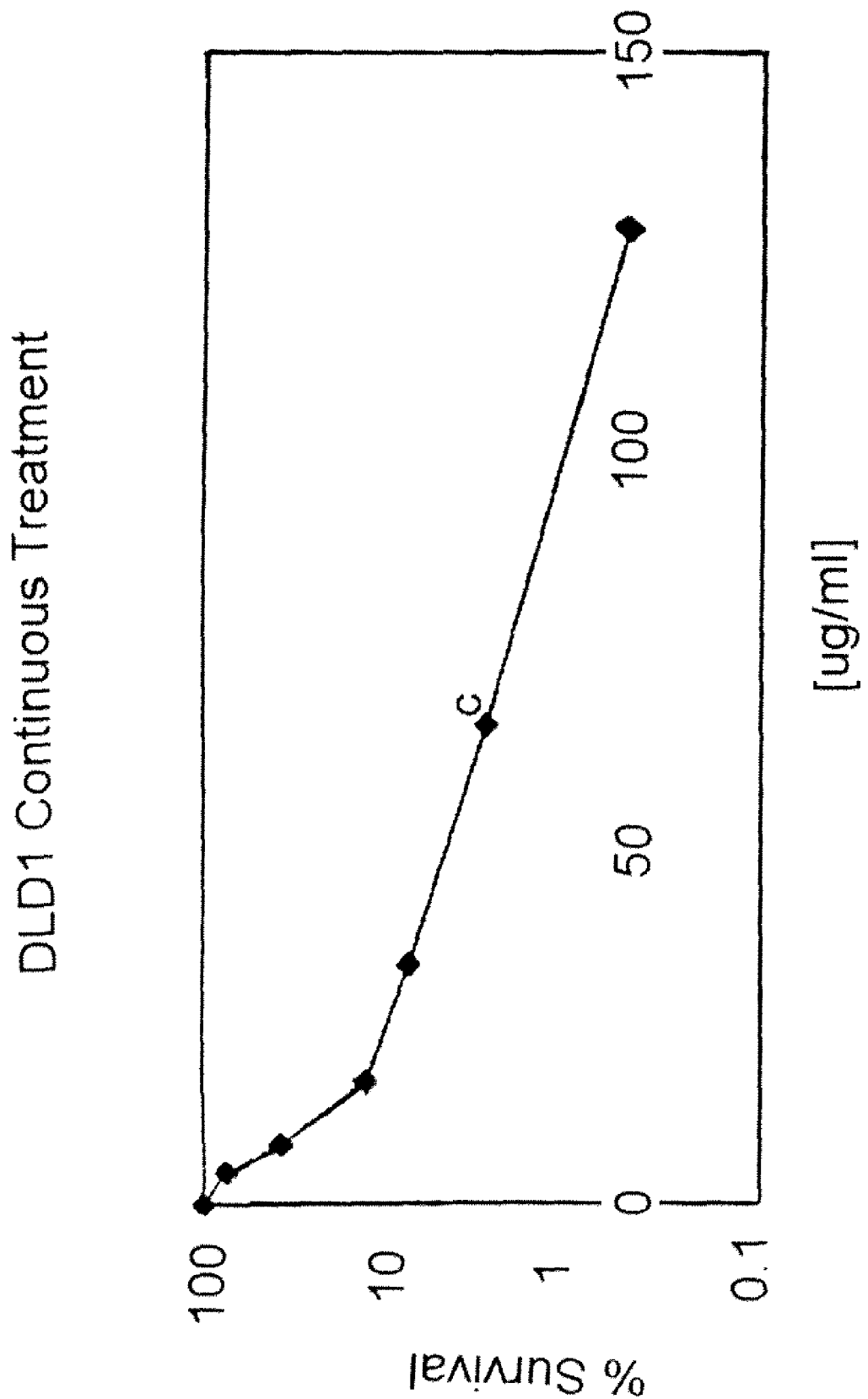

DRUG FOR TREATMENT OF COLON CANCER

This application claims benefit of 61/288,517, Dec. 21, 2009.

BACKGROUND OF THE INVENTION

The present invention relates to the discovery of two new chemicals that can be used for the treatment, prevention, or amelioration of hyperproliferative diseases and/or disorders such as cancer. It finds particular application in conjunction with cancer such as colon cancer, and will be described with particular reference thereto.

Hyperproliferation is used to describe aberrant/dysregulated cellular growth, a hallmark of diseases like cancer. Currently, cancer therapy may involve surgery, chemotherapy, hormonal therapy and/or radiation treatment to eradicate neoplastic cells in a patient (see, for example, Stockdale, 1998, "Principles of Cancer Patient Management", in Scientific American: Medicine, vol. 3, Rubenstein and Federman, eds., Chapter 12, Section IV). Recently, cancer therapy could also involve biological therapy or immunotherapy. All of these approaches pose significant drawbacks for the patient. Surgery, for example, may be contraindicated due to the health of the patient or may be unacceptable to the patient. Additionally, surgery may not completely remove the neoplastic tissue. Radiation therapy is only effective when the neoplastic tissue exhibits a higher sensitivity to radiation than normal tissue, and radiation therapy can also often elicit serious side effects. Hormonal therapy is rarely given as a single agent and although can be effective, is often used to prevent or delay recurrence of cancer after other treatments have removed the majority of the cancer cells. Biological therapies/immunotherapies are limited in number and may produce side effects such as rashes or swellings, flu-like symptoms, including fever, chills and fatigue, digestive tract problems or allergic reactions.

With respect to chemotherapy, many potential drugs have been discovered in the last 30 years for treating hyperproliferative disease and/or disorder such as cancer. Actually, a large number of different cancers are treated successfully and produce strong remissions that often prevent the cancers from regaining strength. The mechanisms by which these results are obtained are to kill the cells by interfering with the reproductive machinery of cell replication. For example, standard cancer chemotherapeutic drugs kill cancer cells upon induction of programmed cell death ("apoptosis") by targeting basic cellular processes and molecules. These basic cellular processes and molecules include RNA/DNA (alkylating and carbamylating agents, platin analogs and topoisomerase inhibitors), metabolism (drugs of this class are named antimetabolites and examples are folic acid, purin and pyrimidine antagonist) as well as the mitotic spindle apparatus with αβ-tubulin heterodimers as the essential component (drugs are categorized into stabilizing and destabilizing tubulin inhibitors; examples are Taxol/Paclitaxel®, Docetaxel/Taxotere® and vinca alkaloids). A significant majority of cancer chemotherapeutics act by inhibiting DNA synthesis, either directly, or indirectly by inhibiting the biosynthesis of the deoxyribonucleotide triphosphate precursors, to prevent DNA replication and concomitant cell division (see, for example, Gilman et al., Goodman and Gilman's: The Pharmacological Basis of Therapeutics, Eighth Ed. (Pergamom Press, New York, 1990)). These agents, which include alkylating agents, such as nitrosourea, anti-metabolites, such as methotrexate and hydroxyurea, and other agents, such as etoposides, campathecins, bleomycin, doxorubicin, daunorubicin, etc., although not necessarily cell cycle specific, kill cells during S phase because of their effect on DNA replication. Other agents, specifically colchicine and the vinca alkaloids, such as vinblastine and vincristine, interfere with microtubule assembly resulting in mitotic arrest.

Despite the availability of a variety of chemotherapeutic agents, chemotherapy has many drawbacks (see, for example, Stockdale, 1998, "Principles Of Cancer Patient Management" in Scientific American Medicine, vol. 3, Rubenstein and Federman, eds., ch. 12, sect. 10). Almost all chemotherapeutic agents are toxic, and chemotherapy causes significant, and often dangerous, side effects, including severe nausea, bone marrow depression, immunosuppression, etc. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even those agents that act by mechanisms different from the mechanisms of action of the drugs used in the specific treatment; this phenomenon is termed pleiotropic drug or multidrug resistance. Thus, because of drug resistance, many cancers prove refractory to standard chemotherapeutic treatment protocols.

Because some of these drugs are carefully designed to interfere with the replication of fast growing cells, they also often interfere with the replication of those non-carcinogenic cells that also constantly replicate, such as hair, gut lining and so on. As a result, these drugs have to be used at low doses in order to minimize the terrifying effects of the treatments. The challenge is therefore how to create potent and specific cancer cells killing agents, or inhibiting agents with minimal side effects, and, notably without killing other reproducing cells.

Advantageously, the invention provides a method for treating, preventing or ameliorating a hyperproliferative disease and/or disorder such as cancer with minimal or none of the side effects often associated with chemotherapy. By not killing normal reproducing cells, drugs which do not exhibit high potency can be used at large doses which might still be sufficient to realize the medical objective.

BRIEF DESCRIPTION OF THE INVENTION

A first aspect of the invention provides a method for treating, preventing or ameliorating a hyperproliferative disease and/or disorder in a mammal comprising administering to the mammal a therapeutically effective amount of one or more compounds selected from the group consisting of compounds of Formula (1) or (2); or a pharmaceutically acceptable salt or metabolite thereof.

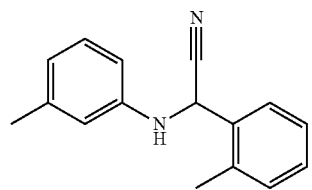

Formula (1)

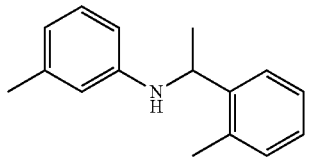

Formula (2)

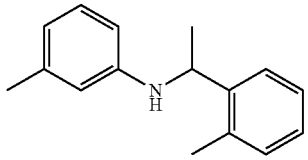

Formula (2)

BRIEF DESCRIPTION OF THE DRAWINGS

FIG. 1 illustrates the survival percentage colon DLD-1 carcinoma cells in mice after continuous treatment with Formula (2).

DETAILED DESCRIPTION OF THE INVENTION

As used herein, the term "pharmaceutically acceptable" means approved by a regulatory agency of the Federal or a state government or listed in the U.S. Pharmacopeia or other generally recognized pharmacopeia for use in animals, and more particularly in humans.

As used herein, a "therapeutically effective amount" refers to that amount of the therapeutic agent sufficient to destroy, modify, control or remove a hyperproliferative disease and/or disorder such as primary, regional or metastatic cancer tissue. A therapeutically effective amount may refer to the amount of therapeutic agent sufficient to delay or minimize the spread of cancer. A therapeutically effective amount may also refer to the amount of the therapeutic agent that provides a therapeutic benefit in the treatment or management of cancer. Further, a therapeutically effective amount with respect to a therapeutic agent means that amount of therapeutic agent alone, or in combination with other therapies, that provides a therapeutic benefit in the treatment or management of cancer, including the amelioration of symptoms associated with the disease being treated.

In various exemplary embodiments, the invention provides a method for treating, preventing or ameliorating a hyperproliferative disease and/or disorder in a mammal comprising administering to the mammal a therapeutically effective amount of one or more compounds selected from the group consisting of the compounds of Formula (I) (MOL_ID_6) or a pharmaceutically acceptable salt or metabolite thereof.

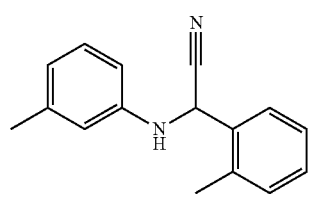

Formula (1)

In another embodiment, the invention provides a method for treating, preventing or ameliorating a hyperproliferative disease and/or disorder in a mammal comprising administering to the mammal a therapeutically effective amount of one or more compounds selected from the group consisting of the compounds of Formula (2) (MOL_ID_7) or a pharmaceutically acceptable salt or metabolite thereof.

In various exemplary embodiments, the invention may be used to treat, prevent or ameliorate a hyperproliferative disease and/or disorder such as cancer. Exemplary cancers may be selected from the group consisting of cancer of the breast, bladder, bone, brain, central and peripheral nervous system, colon, endocrine glands, esophagus, endometrium, germ cells, head and neck, kidney, liver, lung, larynx and hypopharynx, mesothelioma, sarcoma, ovary, pancreas, prostate, rectum, renal, small intestine, soft tissue, testis, stomach, skin, ureter, vagina and vulva; inherited cancers, retinomblastoma and Wilms tumor; leukemia, lymphoma, non-Hodgkins disease, chronic and acute myeloid leukaemia, acute lymphoblastic leukemia, Hodgkins disease, multiple myeloma and T-cell lymphoma; myelodysplastic syndrome, plasma cell neoplasia, paraneoplastic syndromes, cancers of unknown primary site and AIDS related malignancies.

The compounds of Formula (1); 2-(m-toluidino)-2-o-tolylacetonitrile and Formula (2); 3-methyl-N-(1-o-tolylethyl) benzenamine, as well as a pharmaceutically acceptable salt or metabolite thereof may be useful for treating, preventing or ameliorating include, but are not limited to, colon cancer, leukemia, such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer, including, but not limited to, adenocarcinoma, lobular (small cell) carcinoma, intraductal carcinoma, medullary breast cancer, mucinous breast cancer, tubular breast cancer, papillary breast cancer, primary cancers, Paget's disease, and inflammatory breast cancer, adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma basal cell carcinoma, sarcoma, and Paget's disease; cervical cancers such as but not limited to, squamous cell carcinoma, and adenocareinoma; uterine cancers such as but not limited to endometrial carcinoma and uterine sarcoma, ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoetidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, non-seminoma, embryonal carcinoma, teratoma carcinoma, choriocarcinoma (yolk-sac tumor), prostate cancers such as but hot limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, further cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagitosis, Treatment, and Recovery; Viking Penguin, Penguin Books U.S.A. Inc. United States of America). However, the compounds in Formulas (1) and (2) are particularly useful in the treatment of colon cancer.

In various exemplary embodiments, many cell lines can be subject to the method according to the present invention, for example, Colon Cancer such as DLD-1, COLO 205, HCC-2998, HCT-116, HCT-15, HT29, KM12, and SW-620; Leukemia such as CCRF-CEM, HL-60(TB), K-562, MOLT-4, RPMI-8226, and SR; Non-Small Cell Lung Cancer such as A549/ATCC, EKVX, HOP-62, HOP-92, NCI-H226, NCI-H23, NCI-H322M, NCI-H460, and NCI-H522; CNS Cancer such as SF-268, SF-295, SF-539, SNB-19, SNB-75, and U251; Melanoma such as LOX IMVI, MALME-3M, M14, MDA-MB-435, SK-MEL-2, SK-MEL-28, SK-MEL-5, UACC-257, and UACC-62; Ovarian Cancer such as IGROV1, OVCAR-3, OVCAR-4, OVCAR-5, OVCAR-8, NCI/ADR-RES, and SK-OV-3; Renal Cancer such as 786-0, A498, ACHN, CAKI-1, RXF 393, SN12C, TK-10, and UO-31; Prostate Cancer such as PC-3 and DU-145; Breast Cancer such as MCF7, MDA-MB-231/ATCC, HS 578T, BT-549, and T-47D.

In various exemplary embodiments, the compound of Formulas (1) or (2), or a pharmaceutically acceptable salt or metabolite thereof is administered as a pharmaceutical composition. Additional ingredients in the pharmaceutical composition may be selected from for example a pharmaceutically acceptable excipient, diluent and/or carrier, among others. A person skilled in the art is familiar with auxiliaries, vehicles, excipients, diluents, carriers or adjuvants which are suitable for the desired pharmaceutical formulations, preparations or compositions on account of his/her expert knowledge. For example, pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. Water is a preferred vehicle when the compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propyleneglycol, water, ethanol and the like. The present compositions, if desired, can also contain minor amounts of wetting or emulsifying agents, or pH buffering agents. In addition to solvents, gel formers, ointment bases and other active compound excipients, for example antioxidants, dispersants, emulsifiers, preservatives, solubilizers, colorants, complexing agents or permeation promoters, can be used.

In addition to the compounds of Formula (1) and (2), or a pharmaceutically acceptable salt or metabolite thereof, the pharmaceutical composition may contain other therapeutic agent such as an anti-inflammatory agent. Examples of anti-inflammatory agents include, but are not limited to, steroids (e.g., cortisol cortisone, fludrocortisone, prednisone, 6a-methylprednisone, triamcinolone, betamethasone or dexamethasone), nonsteroidal antiinflammatory drugs (NSAIDS (e.g., aspirin, acetaminophen, tolmetin, ibuprofen, mefenamic acid, piroxicam, nabumetone, rofecoxib, celecoxib, etodolac or nimesulide). In another embodiment, the other therapeutic agent is an antibiotic (e.g., vancomycin, penicillin, amoxicillin, ampicillin, cefotaxime, ceftriaxone, cefixime, rifampinmetronidazole doxycycline or streptomycin). In another embodiment, the other therapeutic agent is a PDE4 inhibitor (e.g., roflumilast or rolipram). In another embodiment, the other therapeutic agent is an antihistamine (e.g., cyclizine, hydroxyzine, promethazine or diphenhydramine). In another embodiment, the other therapeutic agent is an anti-malarial (e.g., artemisinin, artemether, artsunate, chloroquine phosphate, mefloquine hydrochloride, doxycycline hyclate, proguanil hydrochloride, atovaquone or halofantrine). In one embodiment, the other therapeutic agent is drotrecogin alfa.

The term "mammal" includes an animal (e.g., cow, horse, sheep, pig, chicken, turkey, quail, cat, dog, mouse, rat, rabbit or guinea pig); a non-primate and a primate (e.g., monkey, baboon, chimpanzee and human). The compound of Formulas (1), (2), or pharmaceutically acceptable salt or metabolite thereof may be used as human and veterinary medicine. In various embodiments, the mammal subject to the method according to the invention is a human patient such as an infant, child, adolescent or adult.

Without being bound by any particular theory, the present invention is believed to modulate apoptosis and/or aberrant cell growth in the therapy of benign or malignant neoplastic diseases, such as cancer.

The administration of the compound of Formula (1), (2), or a pharmaceutically acceptable salt or metabolite thereof may be performed in any of the generally accepted modes of administration available in the art. Illustrative examples of suitable modes of administration include intravenous, oral, nasal, parenteral, topical, transdermal and rectal delivery.

The compound of Formula (1), (2), or a pharmaceutically acceptable salt or metabolite thereof can be administered to animals (including humans) orally or parenterally in conventional and well known preparations, such as capsules, microcapsules, tablets, granules, powder, troches, pills, suppositories, injections, suspensions and syrups. Suitable formulations in this regard may be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylprrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous sicilic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinyl pyrrolidone or aluminum stearate), a dispersing agent (e.g., hydroxypropylmethylcellulose), a diluent (e.g., water), and/or a base wax (e.g., cocoa buffer, white petrolatum or polyethylene glycol). The compound of Formula (1), (2), or pharmaceutically acceptable salt thereof can also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, e.g., encapsulation in liposomes, microparticles, microcapsules, capsules, etc., and can be used to administer a compound of the invention. Methods of administration include but are not limited to intradermal, intramuscular, intraperitoneal, intravenous, subcutaneous, epidural, oral, sublingual, intranasal, intracerebral, intravaginal, transdermal, rectally, by inhalation, or topically, particularly to the ears, nose, eyes, or skin. The preferred mode of administration is left to the discretion of the practitioner, and will depend in-part upon the site of the medical condition. In most instances, administration will result in the release of the compound into the bloodstream.

In specific embodiments, it may be desirable to administer one or more of the compound of Formula (1), (2), or a pharmaceutically acceptable salt or metabolite thereof locally to the area in need of treatment. This can be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material including membranes, such as sialastic membranes, or fibers. In one embodiment, administration can be by direct injection at the site (or former site) of an atherosclerotic plaque tissue.

The compound of Formula (1), (2), or a pharmaceutically acceptable salt or metabolite thereof of the invention can be delivered in a controlled release system. In one embodiment, a pump may be used (see Langer, supra; Sefton, 1987, CRC Crit. Ref. Biomed. Eng. 14:201; Buchwald et al., 1980, Surgery 88:507 Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, 1983, J. Macronol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In an embodiment, a controlled-release system can be placed in proximity of the target of the compound, e.g., the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, 1990. Science 249:1527-1533) may be used.

In an embodiment, the compound of Formula (1), (2), or a pharmaceutically acceptable salt or metabolite thereof is administered orally. Compositions for oral delivery may be in the form of tablets, lozenges, aqueous or oily suspensions, granules, powders, emulsions, capsules, syrups, or elixirs, for example. Orally administered compositions may contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

In an embodiment, the compound of Formula (1), (2), or a pharmaceutically acceptable salt or metabolite thereof is administered parenterally.

In an embodiment, the compound of Formula (1), (2), or a pharmaceutically acceptable salt or metabolite thereof is administered intravenously, intramuscularly, intradermally or subcutaneously. In a preferred embodiment, the compound is formulated in accordance with routine procedures as a pharmaceutical composition adapted for intravenous administration to human beings. Typically, the compound for intravenous administration is a solution in sterile isotonic aqueous buffer. Where necessary, the composition can also include a solubilizing agent. Compositions for intravenous administration may optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent.

In an embodiment, the compound of Formula (1), (2), or a pharmaceutically acceptable salt or metabolite thereof is administered by infusion. Where the compound is to be administered by infusion, it can be dispensed, for example, with an infusion bottle containing sterile pharmaceutical grade water or saline.

For the treatment of dermatoses, the compound of Formula (1), (2), or a pharmaceutically acceptable salt or metabolite thereof can be in particular administered in the form of those pharmaceutical compositions which are suitable for topical application. For the production of the pharmaceutical compositions, the compounds are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

Without being bound by theory, it is expected that the compound of Formula (1), (2), or a pharmaceutically acceptable salt or metabolite thereof is administered daily. However, the choice of the optimal dosage regime and duration of medication, particularly the optimal dose and manner of administration of the active compounds necessary in each case can be determined by a person skilled in the art on the basis of his/her expert knowledge. The amount of the compound of Formula (1), (2), or pharmaceutically acceptable salt or metabolite thereof in a dosage form may differ depending on factors such as, but not limited to, the route by which it is to be administered to patients. The dosage of the invention can be carried out in the order of magnitude customary for inhibitors of cellular hyperproliferation or apoptosis inducers.

The compound of the invention may also be used in combination therapy with other active compounds. The term "combination" according to this invention may be present as a fixed combination, a non-fixed combination or a kit-of-parts. A "fixed combination" is defined as a combination of the compound of the invention and other active compounds in one unit dosage or in a single entity. One example of a "fixed combination" is a pharmaceutical composition wherein the compound of the invention and other active compounds are present in admixture for simultaneous administration, such as in a formulation. A "kit-of-parts" is defined as a combination wherein the compound of the invention and other active compounds are present in more than one unit. One example of a "kit-of-parts" is a combination wherein the compound of the invention and other active compounds are present separately. The components of the kit-of-parts may be administered separately, sequentially, simultaneously, concurrently or chronologically staggered.

Depending upon the particular disease to be treated or prevented, additional therapeutic active agents, which are normally administered to treat or prevent that disease, may optionally be co-administered. As used herein, additional therapeutic agents that are normally administered to treat or prevent a particular disease are known as appropriate for the disease being treated. For example, compound of the invention thereof may be combined with one or more known anti-cancer agents, such as e.g. with one or more chemotherapeutic and/or target specific anti-cancer agents as described below.

The compounds according to this invention may be administered in combination therapy separately, sequentially, simultaneously, concurrently or chronologically staggered (such as e.g. as combined unit dosage forms, as separate unit dosage forms, as adjacent discrete unit dosage forms, as fixed or non-fixed combinations, as kit-of-parts or as admixtures) with one or more standard therapeutics, in particular art-known anti-cancer agents (chemotherapeutic and/or target specific anti-cancer agents), such as e.g. any of those mentioned above.

The compound of this invention exhibits inhibition of cell proliferation, i.e. they can retard the growth of and/or kill a cell contacted with that compound as compared to cells not contacted with that compound. Most preferable this inhibition of cell proliferation is 100%, meaning that proliferation of all cells is stopped and/or cells undergo programmed cell death.

The method according to the present invention is expected to inhibit cancer cell proliveration yet demonstrates significant absence of side effects, low toxicity, superior bioavailability in general (such as e.g. good enteral absorption), superior therapeutic window, and/or further beneficial effects related with their therapeutic and pharmaceutical suitability.

Accordingly, utilizing the compounds of the present invention may avoid side effects from chemotherapy including, but are not limited to, gastrointestinal toxicity such as, but not limited to, early and late-forming diarrhea and flatulence; nausea; vomiting; anorexia; leukopenia; anemia; neutropenia; asthenia; abdominal cramping; fever; pain; loss of body weight; dehydration; alopecia; dyspnea; insomnia; dizziness, mucositis, xerostomia, and kidney or renal failure, as well as constipation, nerve and muscle effects, temporary or permanent damage to kidneys and bladder, flu-like symptoms, fluid retention, and temporary or permanent infertility.

The subject compositions are now further described with reference to the following non-limiting examples:

Example 1

2-o-tolyl-2-(m-tolylamino)acetonitrile (XXX)

To a flame-dried 25 mL round-bottom flask equipped with a magnetic stirring bar was added m-toluidine (365 mg, 3.4 mmol), o-tolualdehyde (391 mg, 3.3 mmol) and 5 mL of dry acetonitrile. The solution was stirred to make a homogeneous solution, then trimethylsilyl cyanide (480 µL, 3.6 mmol) was added and the solution stirred at room temperature for 23 h. The reaction was quenched by adding 5.5 mL satureated ammonium chloride solution and allowed to vent. The reaction mixture was extracted with ethyl acetate, dried over anhydrous magnesium sulfate, filtered, and concentrated to give the crude product (50% dichloromethane/hexanes, Rf=0.025). The crude was dissolved in a minimal amount of boiling toluene, a 4-5 fold volume of hexanes added and the solution allowed to sit for several hours, filtered, and dried to give XXX (531 mg, 68.1% yield) as a crystalline solid. Approximately 400 mg of the recrystallized material was additionally purified by flash chromatography using 50% dichloromethane/hexanes, which, after concentration, gave XXX as a white crystalline solid (m.p. 103-104° C.).

$^1$H NMR (400 MHz, CDCl$_3$) δ 7.71 (d, J=7.1 Hz, 1H), 7.40-7.29 (m, 1H), 7.26 (d, J=8.4 Hz, 1H), 3.77 (d, J=8.4 Hz,

1H), 2.36 (d, J=20.6 Hz, 6H); $^{13}$C NMR (100 MHz, CDCl$_3$) δ 145.05, 139.77, 136.72, 132.33, 131.52, 129.96, 129.96, 129.70, 127.14, 121.30, 118.67, 114.76, 114.76, 111.17, 48.29, 21.87, 18.91.

Example 2

3-methyl-N-(1-o-tolylethyl)aniline (ZZZ)

To a flame-dried 100 mL round-bottom flask equipped with a magnetic stirring bar was added 260 mg of decaborane (260 mg, 2.1 mmol), dry methanol (52 mL), m-toluidine (780 μL, d=0.989 g/mL, 7.2 mmol), and 2'-methylacetophenone (1 mL, d=1.014 g/mL, 7.6 mmol), and the mixture stirred and monitored by TLC (product Rf=0.43-0.44 in 50% dichloromethane/hexanes). The solution gradually changed color from brown to pale yellow and the reaction proceeded. After 20 hours, the solution was colorless, decaborane (115 mg, 0.941 mmol) was added, at which time the solution became pale yellow again. Another portion of decaborane (103 mg, 0.843 mmol) was added after 4 days, and the reaction stirred an additional six days. After completion, the solvent was evaporated, the residue redissolved, loaded onto a short 2.5 inch columns of silica gel and eluted with 5% ethyl acetate/hexanes. The eluent was collected and concentrated, and the crude product purified by flash chromatography using a slow gradient of 10% dichloromethane/hexanes to 20% dichloromethane/hexanes. Fractions were combined and concentrated to give the desired product ZZZ (1.29 g, 79.6%) as colorless oil.

$^1$H NMR (400 MHz, CDCl$_3$) δ 7.47-7.35 (m, 1H), 7.20-7.07 (m, 3H), 6.96 (t, J=7.5 Hz, 1H), 6.46 (d, J=7.5 Hz, 1H), 6.37-6.16 (m, 2H), 4.65 (q, J=6.6 Hz, 1H), 2.43 (s, 3H), 2.21 (s, 3H); 1.46 (d, J=6.6 Hz, 3H), 1.25 (s, 1H); $^{13}$C NMR (100 MHz, CDCl$_3$) δ 147.48, 143.05, 139.05, 134.81, 130.77, 129.27, 126.87, 126.79, 124.88, 118.37, 114.18, 110.16, 49.95, 23.87, 19.23.

FIG. 1 illustrates the results of an in vitro test with cancerous DLD1 colon cells treated continuously with Formula (2). The survival percentage for DLD-1 cells decreases from 100 percent without treatment to less than 1 percent in the presence of continuous treatment of about 125 μg·ml of Formula (2).

The exemplary embodiments have been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A method for treating or ameliorating colon cancer in a mammal comprising identifying the presence of said colon cancer in the mammal and administering a therapeutically effective amount of one or more compounds selected from the group consisting of compounds of Formula (1), (2), and a pharmaceutically acceptable salt thereof to said mammal:

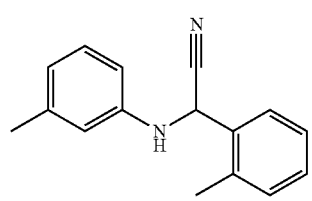

Formula (1)

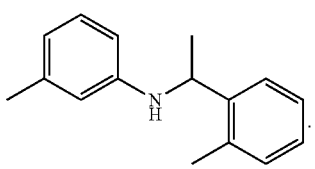

Formula (2)

2. The method according to claim 1, in which the compound or pharmaceutically acceptable salt thereof is administered as a pharmaceutical composition.

3. The method according to claim 2, in which the pharmaceutical composition further comprises a pharmaceutically acceptable excipient, diluent and/or carrier.

4. The method according to claim 1, in which the mammal is a human.

5. The method according to claim 1, in which the compound or pharmaceutically acceptable salt thereof is administered orally.

6. The method according to claim 1, in which the compound or pharmaceutically acceptable salt thereof is administered parenterally.

7. The method according to claim 1, in which the compound or pharmaceutically acceptable salt thereof is administered intravenously, intramuscularly, intradermally or subcutaneously.

8. The method according to claim 1, in which the compound or pharmaceutically acceptable salt thereof is administered by infusion.

9. The method according to claim 1, in which the compound or pharmaceutically acceptable salt thereof is administered daily.

* * * * *